United States Patent
Guo et al.

(10) Patent No.: US 7,214,857 B2
(45) Date of Patent: May 8, 2007

(54) NO-APICAL MERISTEM PROTEINS, POLYNUCLEOTIDES AND METHODS OF USE FOR SAME

(75) Inventors: Mei Guo, West Des Moines, IA (US); Mary A. Rupe, Altoona, IA (US); Olga Danilevskaya, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 547 days.

(21) Appl. No.: 10/438,969

(22) Filed: May 15, 2003

(65) Prior Publication Data

US 2003/0226167 A1   Dec. 4, 2003

Related U.S. Application Data

(60) Provisional application No. 60/381,248, filed on May 16, 2002.

(51) Int. Cl.
| | |
|---|---|
| *A01H 1/00* | (2006.01) |
| *C07H 21/04* | (2006.01) |
| *C07K 14/415* | (2006.01) |
| *C12N 5/14* | (2006.01) |
| *C12N 9/00* | (2006.01) |

(52) U.S. Cl. .................. 800/295; 435/6; 435/69.1; 435/468; 435/419; 435/252.3; 435/320.1; 530/370; 536/23.6; 800/278

(58) Field of Classification Search .............. 435/6, 435/69.1, 468, 419, 252.3, 320.1, 183; 530/370; 536/23.6; 800/278, 295

See application file for complete search history.

(56) References Cited

U.S. PATENT DOCUMENTS

2004/0025202 A1* 2/2004 Laurie et al. ............... 800/281

FOREIGN PATENT DOCUMENTS

| WO | WO 00/47742 | 8/2000 |
|---|---|---|
| WO | WO 2005/024017 | 3/2005 |

OTHER PUBLICATIONS

Souer et al. Cell, vol. 85, pp. 159-170, 1996.*
Laurie et al., N_Geneseq_21 database, Accession No. ADJ48225, Seq Id No:229.*
Kreps et al., N_Geneseq_21 database; Accession No. ACL33862, Seq Id No:12425.*
Kikuchi, K., et al.; "Molecular analysis of the NAC gene family in rice"; Mol Gen Genet (2000) 262:1047-1051.

Zimmerman, R., et al.; "Pattern fromation in the monocot embryo as revealed by NAM and CUC3 orthologues from Zea mays L."; Plant Molecular Biology (2005) 58:669-685.
Guo, M., et al.; "Genome-wide mRNA profiling reveals heterochronic allelic variation and a new imprinted gene in hybrid maize endosperm"; The Plant Journal (2003) 36:30-44.
Aida, M., et al.; "Genes Involved in Organ Separation in Arabidopsis: An Analysis of the cup-shaped cotyledon Mutant"; The Plant Cell (1997) 9:841-857.
Souer, E., et al.; "The No Apical Meristem Gene of Petunia Is Required for Pattern Formation in Embyros and Flowers and Is Expressed at Meristem and Primordia Boundries"; Cell (1996) 85:159-170.
Koes, R., et al.; "Targeted gene inactivation in petunia by PCR-based selection of transposon insertion mutants"; Proc.Natl. Acad. Sci. USA (1995) 92:8149-8153.
Souer, E., et al.; "A general method to isolate genes tagged by a high copy No. transposable element"; The Plant Journal (1995) 7(4):677-685.
Souer, E., et al.; "Genetic Control of branching pattern and floral identiy during Petunia inflorescence development"; Development (1998) 125:733-742.
Itoh, J-I., et al.; "Shoot Organization Genes Regulate Shoot Apical Meristem Organization and the Pattern of Leaf Primordium Initiation in Rice"; (2000) 12:2161-2174.
Evans, M.M.S.; "Genetics of Angiosperm Shoot Apical Meristem Development"; Annu. Rev. Plant Physiol. Plant Mol. Biol.; (1997) 48:673-701.
Database EMBL Online—"605075E02.x1 605—Endosperm cDNA library from Schmidt lab Zea mays cDNA, mRNA sequence."Jun. 28, 1999.
Database EMBL Online—"5c08c10 membrane-free polysomes from endosperm Zea mays cDNA, clone 5c08c10 5'end, mRNA sequence." Jul. 21, 1994.

* cited by examiner

*Primary Examiner*—Phuong T. Bui
(74) *Attorney, Agent, or Firm*—Pioneer Hi-Bred Int'l Inc

(57) ABSTRACT

The present invention provides polynucleotides and related polypeptides of the protein ZMNAM isolated from maize endosperm. The invention provides genomic sequence for the ZMNAM gene. ZMNAM is a novel gene and is regulated by gene-specific imprinting. ZMNAM expression is endosperm-specific and expressed throughout the endosperm development, peaking at 25 DAP. Genomic imprinting has been implicated to play a role in endosperm development. Genes regulated by allele-specific imprinting are suspected to be non-essential to seed development. Gene-specific imprinting however, regulates developmentally important genes. The ZMNAM gene, a putative transcriptional factor, may play an important role in endosperm development, which may further affect kernel size, plant vigor during germination and at the early seedling stage.

8 Claims, 5 Drawing Sheets

FIGURE 3

NO-APICAL MERISTEM PROTEINS, POLYNUCLEOTIDES AND METHODS OF USE FOR SAME

CROSS REFERENCE

This utility application claims the benefit U. S. Provisional Application No. 60/381,248, filed May 16, 2002, which is incorporated herein by reference.

FIELD OF THE INVENTION

The invention relates generally to the fields of agriculture and molecular biology. More specifically, the invention relates to the isolation of a novel polynucleotide from maize.

BACKGROUND OF THE INVENTION

The double fertilization process of flowering plants results in a diploid embryo and a triploid endosperm tissue, which are otherwise genetically identical. Endosperm has 2 n of the maternal genome and 1 n of the paternal genome. It has been shown that such a unique genetic composition is important to normal seed development (Rhoades and Dempsey, *Genetics* 54:505–22 (1966); Lin, *Genetics* 107:103–15 (1984); Scott et al., *Development* 125:3329–41 (1998)).

The parental-origin-specific modification of a gene can cause various effects on the expression of the two parental alleles in the offspring. Among various parental effects, genomic imprinting, in which expression of the gene is dependent on the parental source of its transmission, is the most studied. Imprinting is a developmental phenomenon wherein a gene in a gamete or zygote is modified such that preferential expression of a single parental allele occurs in the offspring. The definition of genomic imprinting does not necessarily require monoallelic expression; instead, both alleles may be expressed but expressed unequally (Feinberg, *Curr. Top. Microbiol. Immunol.* 249:87–99 (2000)).

Limited information is available at the gene expression level about the differences between the parental genomes, such as transcription activation and regulation of the maternal and paternal genomes after the union of the central and sperm cell and during endosperm development. To date, only a few genes demonstrating imprinting effects have been found in plants. Some of the imprinted genes include R, a transcription factor involved in the anthocyanin pigment pathway of maize; dzr1, which conditions low accumulation of the 10-kDa zein in maize endosperm; MEA and FIE, similar to Drosophila polycomb proteins; and FIS2, a DNA-binding transcriptional regulatory protein in Arabidopsis (Kermicle, *Genetics* 66:69–85 (1970); Chaudhuri and Messing, *Proc. Natl. Acad. Sci. USA* 91:4867–71 (1994); Grossniklaus et al., Science 280:235–41 (1998); Luo et al., *Proc. Natl. Acad. Sci USA* 96:296–301 (1999); and Luo et al., *Proc. Natl. Acad. Sci USA* 97:10637–42 (2000)). All of the imprinted genes identified in plants to date involved inactivation of the paternal allele and were associated with endosperm tissue, although there are inconsistencies in reporting whether MEA affects embryo tissue (Kinoshita et al., *The Plant Cell* 11:1945–52 (1999)).

In contrast to plants, genes that are expressed from only one of the parental alleles have been well characterized in mammals, where the disturbance of imprinting can result in dramatic developmental aberrations and cancer (Reik and Maher, *Trends Genet* 13(8):330–4 (1997)). In this taxonomic group, approximately 20 genes have been identified as imprinted genes (Bartolomei and Tilghman, *Ann. Rev. Genet* 31:439–525 (1997)). Many of these imprinted genes appear to regulate the expression of developmentally important genes. A recent study reported the parent-of-origin effect on quantitative trait loci (QTLs) for mouse body composition (De Koning et al., *Proc. Natl. Acad. Sci. USA* 97:7947–50 (2000). Four out of five QTLs detected were found subject to imprinting, indicating that genomic imprinting might be a more common phenomenon than previously thought, even for complex traits.

In view of the limited information about imprinted genes in plants, in particular their role in endosperm development, it would be desirable to identify and characterize such genes. Accordingly, the inventors have identified a novel gene in maize endosperm that is imprinted and which shows homology to the Petunia No-Apical Meristem (NAM) gene. NAM (no-apical meristem) has been shown to be required for pattern formation in embryos and flowers, and Petunia embryos carrying the NAM mutation fail to develop a shoot apical meristem (Souer et al., *Cell* 85(2):159–70 (1996)). Shoot apical meristem is a collection of undifferentiated cells set aside during embryogenesis. The production of vegetative structures, such as leaves or shoots, and of reproductive structures, such as flowers, is temporally segregated, such that a leaf or shoot arises early in a plant life cycle, while a flower develops later. The transition from vegetative to reproductive development is the consequence of a process termed floral induction (Yanofsky, *Ann. Rev. Plant Physiol. Plant Mol. Biol.* 46:167–88 (1995)).

Once induced, shoot apical meristem either persists and produces floral meristem, which gives rise to flowers, and lateral meristem, which gives rise to branches, or is itself converted to floral meristem. Floral meristem differentiates into a single flower having a fixed number of floral organs in a whorled arrangement. Dicots, for example, contain four whorls (concentric rings), in which sepals (first whorl) and petals (second whorl) surround stamens (third whorl) and carpels (fourth whorl).

Although shoot meristem and floral meristem both consist of meristemic tissue, shoot meristem is distinguishable from the more specialized floral meristem. Shoot meristem generally is indeterminate and gives rise to an unspecified number of floral and lateral meristems. In contrast, floral meristem is determinate and gives rise to the fixed number of floral organs that comprise a flower.

The NAM gene appears to be a member of a large gene family that is suggested to comprise transcriptional factors important to plant development (Souer et al., supra; Kikuchi et al., *Mol. Gen. Genet* 262(6):1047–51 (2000)).

SUMMARY OF THE INVENTION

The present invention provides polynucleotides, related polypeptides and all conservatively modified variants of a newly discovered NAM sequence from maize. The invention provides the genomic sequence for the ZMNAM gene. ZMNAM is a novel gene and is regulated by gene-specific imprinting. ZMNAM expression is endosperm-specific and expressed throughout the endosperm development, peaking at 25 DAP. Genomic imprinting has been implicated to play a role in endosperm development. Genes regulated by allele-specific imprinting are suspected to be non-essential to seed development. Gene-specific imprinting however, regulates developmentally important genes.

According to the invention, two members of the NAM family have been identified in maize, which are expressed in the endosperm of the plants. Additionally partial sequences of these polynucleotides have been obtained and are disclosed herein as SEQ ID NOS: 1, 2, 3, 4, or 8. The full-length nucleotide sequence of the ZMNAM comprises the sequence found in SEQ ID NO 7, and the genomic sequence is disclosed herein as SEQ ID NO: 5.

ZMNAMs unique gene-specific imprinting and endosperm-specific expression are evidences of its involvement in controlling endosperm growth and kernel size. ZMNAM can therefore be utilized to manipulate the developing endosperm. Because of ZMNAM's gene-specific imprinting and endosperm-specific expression pattern one of skill in the art will recognize its usefulness for a variety of purposes which include, but are not limited to: improved yield, more specifically improved grain weight, and improved germination rates, more specifically through improved seed vigor and stress tolerance.

Therefore, in one aspect, the present invention relates to an isolated nucleic acid comprising an isolated polynucleotide sequence encoding a ZMNAM protein. In a further aspect, the present invention is selected from: (a) an isolated polynucleotide encoding a polypeptide of the present invention; (b) a polynucleotide having at least 70% identity to a polynucleotide of the present invention; (c) a polynucleotide comprising at least 25 nucleotides in length which hybridizes under high stringency conditions to a polynucleotide of the present invention; (d) a polynucleotide comprising a polynucleotide of the present invention; (e) a polynucleotide deposited as ATCC Deposit Nos. PTA-4738 or PTA-4542; and (f) a polynucleotide which is complementary to the polynucleotide of (a) to (e).

In another aspect, the present invention relates to a recombinant expression cassette comprising a nucleic acid as described. Additionally, the present invention relates to a vector containing the recombinant expression cassette. Further, the vector containing the recombinant expression cassette can facilitate the transcription and translation of the nucleic acid in a host cell. The present invention also relates to the host cells able to express the polynucleotide of the present invention. A number of host cells could be used, such as but not limited to, microbial, mammalian, plant, or insect.

In yet another embodiment, the present invention is directed to a transgenic plant or plant cells, containing the nucleic acids of the present invention. Preferred plants containing the polynucleotides of the present invention include but are not limited to maize, soybean, sunflower, sorghum, canola, wheat, alfalfa, cotton, rice, barley, tomato, and millet. In another embodiment, the transgenic plant is a maize plant or plant cells. Another embodiment is the transgenic seeds from the transgenic plant.

This invention also provides an isolated polypeptide comprising (a) a polypeptide comprising at least 70% sequence identity to a polypeptide of the present invention; (b) a polypeptide encoded by a nucleic acid of the present invention; and (c) a polypeptide encoded by the polynucleotide deposited as ATCC Deposit Nos. PTA-4738 or PTA-4542.

Another embodiment of the subject invention is a host cell stably transformed by a polynucleotide construct as described above, and a method of making a polypeptide of a recombinant gene comprising:

a) providing a population of these host cells; and
b) growing the population of cells under conditions whereby the polypeptide encoded by the coding sequence of the expression cassette is expressed;
c) isolating the resulting polypeptide.

A number of expression systems using the said host cells could be used, such as but not limited to, microbial, mammalian, plant, or insect.

BRIEF DESCRIPTION OF THE FIGURES

FIG. 3 show the sequence alignment and expression analysis of the ZMNAM gene with other NAM related proteins. The alignment was done with Vector NTI (Frederick, Md., U.S.A.). Accession numbers for genes used in the alignment are: NAM: X92204, OsNAC1: AB028180.1, OsNAC2: AB028181.1. Black shading: amino acids identical in all four sequences. Gray shading: amino acids identical in two-three sequences. Upper-case letters in the consensus sequence are amino acids identical in all four sequences and lower-case letters are the ones identical in three of the four sequences. Underlined regions correspond to the five NAC domains (Kikuchi et al., 2000).

DETAILED DESCRIPTION OF THE INVENTION

Figure 1:
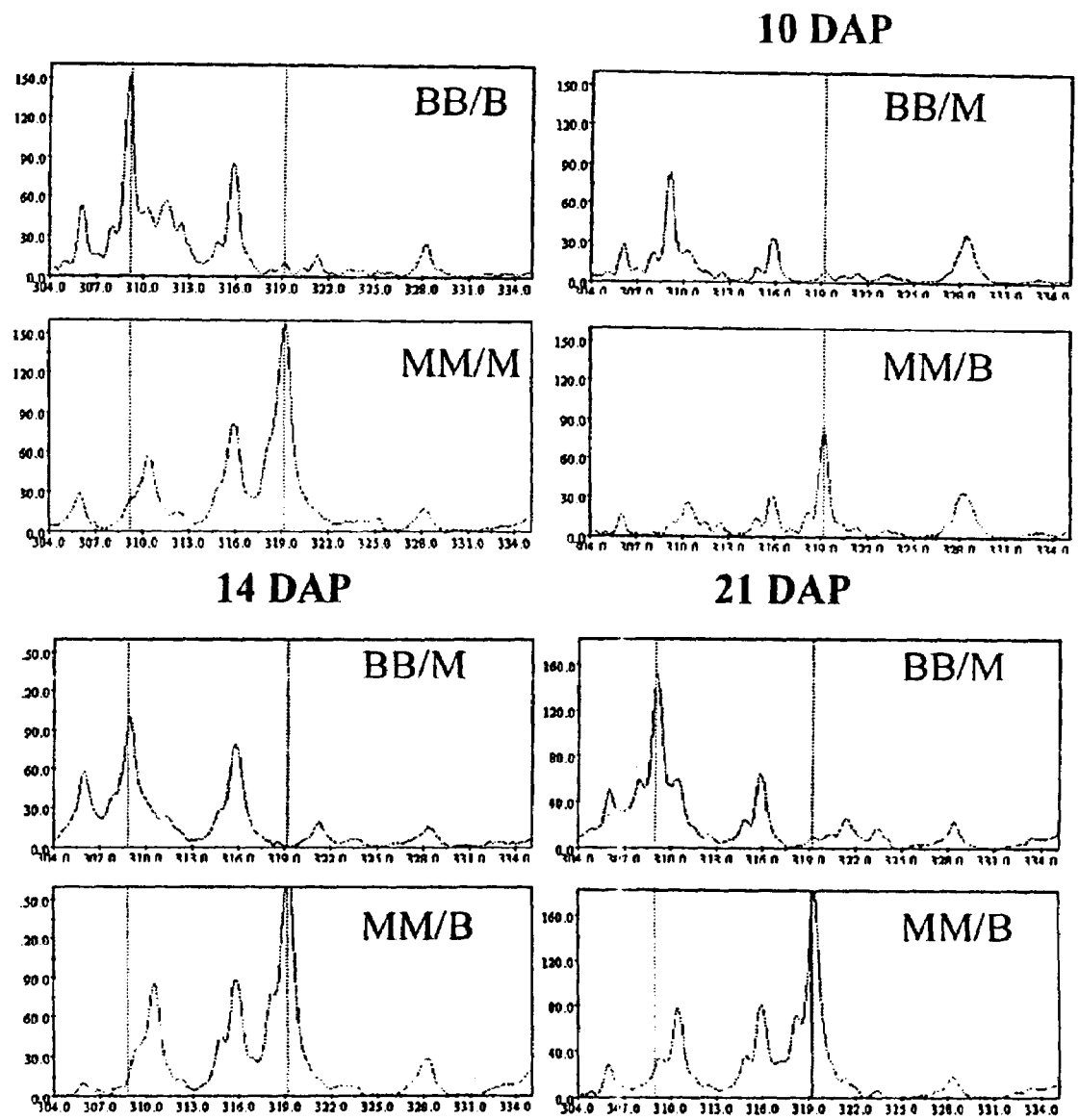
FIG. 1 shows the GeneCalling traces of ZMNAM for the parent (B=B73; M=Mo17), the 10 DAP (days after pollination) hybrid, the 14 DAP hybrid, and the 21 DAP hybrid. The x-axis is the size of the cDNA fragment in base pairs. The y-axis is the level of expression in an arbitrary unit. The vertical lines indicate the corresponding peak of the allele.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, BOTANY: PLANT BIOLOGY AND ITS RELATION TO HUMAN AFFAIRS, John Wiley (1982); CELL CULTURE AND SOMATIC CELL GENETICS OF PLANTS, vol. 1, Vasil, ed. (1984); Stanier et al., THE MICROBIAL WORLD, $5^{th}$ ed., Prentice-Hall (1986); Dhringra and Sinclair, BASIC PLANT PATHOLOGY METHODS, CRC Press (1985); Maniatis et al., MOLECULAR CLONING: A LABORATORY MANUAL (1982); DNA CLONING, vols. I and II, Glover, ed. (1985); OLIGONUCLEOTIDE SYNTHESIS, Gait, ed. (1984); NUCLEIC ACID HYBRIDIZATION, Hames and Higgins, eds. (1984); and the series METHODS IN ENZYMOLOGY, Colowick and Kaplan, eds., Academic Press, Inc., San Diego, Calif.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., DIAGNOSTIC MOLECULAR MICROBIOLOGY: PRINCIPLES AND APPLICATIONS, Persing et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka et al., *J. Gen. Microbiol.* 139:425–32 (1993)) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90%, preferably 60–90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W. H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao et al., *Proc. Natl. Acad. Sci. USA* 82:2306–9 (1985)), or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray et al., *Nucleic Acids Res.* 17:477–98 (1989) and herein incorporated by reference). Thus, the maize preferred codon for a particular amino acid might be derived from known gene sequences from maize. Maize codon usage for 28 genes from maize plants is listed in Table 4 of Murray et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, barley, millet, and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids.

Unless otherwise stated, the term "ZMNAM nucleic acid" means a nucleic acid comprising a polynucleotide ("ZMNAM polynucleotide") encoding a ZMNAM polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, GUIDE TO MOLECULAR CLONING TECHNIQUES, from the series METHODS IN ENZYMOLOGY, vol. 152, Academic Press, Inc., San Diego, Calif. (1987); Sambrook et al., MOLECULAR CLONING: A LABORATORY MANUAL, $2^{nd}$ ed., vols. 1–3 (1989); and CURRENT PROTOCOLS IN MOLECULAR BIOLOGY, Ausubel et al., eds., Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobriychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "ZMNAM polypeptide" refers to one or more amino acid sequences. The term is also inclusive of fragments, variants, homologs, alleles or precursors (e.g., preproproteins or proproteins) thereof. A "ZMNAM protein" comprises a ZMNAM polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60–90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–84 (1984): $T_m$=81.5 ° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part I, chapter 2, "Overview of principles of hybridization and the strategy of nucleic acid probe assays," Elsevier, New York (1993); and CURRENT PROTOCOLS IN MOLECULAR BIOLOGY, chapter 2, Ausubel et al., eds., Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, *Adv. Appl. Math* 2:482 (1981), may conduct optimal alignment of sequences for comparison; by the homology alignment algorithm (GAP) of Needleman and Wunsch, *J. Mol. Biol.* 48:443–53 (1970); by the search for similarity method (Tfasta and Fasta) of Pearson and Lipman, *Proc. Natl. Acad. Sci. USA* 85:2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Version 8 (available from Genetics Computer Group (GCG® programs (Accelrys, Inc., San Diego, Calif).). The CLUSTAL program is well described by Higgins and Sharp, *Gene* 73:237–44 (1988); Higgins and Sharp, *CABIOS* 5:151–3 (1989); Corpet et al., *Nucleic Acids Res.* 16:10881–90 (1988); Huang et al., *Computer Applications in the Biosciences* 8:155–65 (1992), and Pearson et al., *Meth. Mol. Biol.* 24:307–31 (1994). The preferred program to use for optimal global alignment of multiple sequences is PileUp (Feng and Doolittle, *J. Mol. Evol.*, 25:351–60 (1987) which is similar to the method described by Higgins and Sharp, *CABIOS* 5:151–53 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See CURRENT PROTOCOLS IN MOLECULAR BIOLOGY, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff, *Proc. Natl. Acad. Sci. USA* 89:10915 (1989)).

Unless otherwise stated, sequence identity/similarity values provided herein refer to the value obtained using the BLAST 2.0 suite of programs using default parameters (Altschul et al., *Nucleic Acids Res.* 25:3389–402 (1997)).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput Chem.* 17:149–63 (1993)) and XNU (Claverie and States, *Comput. Chem.* 17:191–201 (1993)) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.* 4:11–17 (1988), e.g., as implemented in the program PC/GENE (Intelligenetics, Mountain View, Calif., U.S.A.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50–100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55–100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55–100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The invention discloses novel No-Apical Meristem polynucleotides and polypeptides isolated from maize. The novel nucleotides and proteins of the invention have an expression pattern which indicates that they are developmentally regulated and thus play an important role in plant development. The polynucleotides are expressed in endosperm and are both imprinted. The polynucleotides and polypeptides thus provide an opportunity to manipulate plant endosperm development to alter seed development, seed timing or seed composition. This may be used to create a sterile plant, a seedless plant or a plant with altered endosperm composition.

Nucleic Acids

The present invention provides, inter alia, isolated nucleic acids of RNA, DNA, and analogs and/or chimeras thereof, comprising a ZMNAM polynucleotide.

The present invention also includes polynucleotides optimized for expression in different organisms. For example, for expression of the polynucleotide in a maize plant, the sequence can be altered to account for specific codon preferences and to alter GC content as according to Murray et al, supra. Maize codon usage for 28 genes from maize plants is listed in Table 4 of Murray et al., supra.

The ZMNAM nucleic acids of the present invention comprise isolated ZMNAM polynucleotides which are inclusive of:

(a) a polynucleotide encoding a ZMNAM polypeptide and conservatively modified and polymorphic variants thereof;

(b) a polynucleotide which selectively hybridizes to a polynucleotide of (a);

(c) a polynucleotide having at least 70% sequence identity with polynucleotides of (a) or (b);

(d) complementary sequences of polynucleotides of (a), (b), or (c); and (e) a polynucleotide comprising at least 15 contiguous nucleotides from a polynucleotide of (a), (b), (c), or (d).

Plasmids containing polynucleotide sequences of the invention were deposited with American Type Culture Collection (ATCC), Manassas, Va., and assigned Accession Nos. PTA-4738 and PTA-4542. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II , lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II , pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSIox, and lambda MOSEIox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang et al., *Meth. Enzymol.* 68:90–9 (1979); the phosphodiester method of Brown et al., *Meth. Enzymol.* 68:109–51 (1979); the diethylphosphoramidite method of Beaucage et al., *Tetra. Letts.* 22(20):1859–62 (1981); the solid phase phosphoramidite triester method described by Beaucage et al., supra, e.g., using an automated synthesizer, e.g., as described in Needham-VanDevanter et al., *Nucleic Acids Res.* 12:6159–68 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5'non-coding or untranslated region (5' UTR) of the RNA. Positive sequence motifs include translational initiation consensus sequences (Kozak, *Nucleic Acids Res.* 15:8125 (1987)) and the 5<G>7 methyl GpppG RNA cap structure (Drummond et al., *Nucleic Acids Res.* 13:7375 (1985)). Negative elements include stable intramolecular 5'UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See Devereaux et al., *Nucleic Acids Res.* 12:387–395 (1984)); or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang et al., *Proc. Natl. Acad. Sci. USA* 94:4504–9 (1997); and Zhao et al., *Nature Biotech* 16:258–61 (1998). Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'- promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell et al., *Nature* 313:810–2 (1985); rice actin (McElroy et al., *Plant Cell* 163–171 (1990)); ubiquitin (Christensen et al., *Plant Mol. Biol.* 12:619–632 (1992) and Christensen et al., *Plant Mol. Biol.* 18:675–89 (1992)); pEMU (Last et al., *Theor. Appl. Genet.* 81:581–8 (1991)); MAS (Velten et al., *EMBO J.* 3:2723–30 (1984)); and maize H3 histone (Lepetit et al., *Mol. Gen. Genet.* 231:276–85 (1992); and Atanassvoa et al., *Plant Journal* 2(3):291–300 (1992)); ALS promoter, as described in PCT Application No. WO 96/30530; and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'- end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan et al., *Nucleic Acids Res.* 12:369–85 (1983)); the potato proteinase inhibitor II (PINII) gene (Keil et al., *Nucleic Acids Res.* 14:5641–50 (1986); and An et al., *Plant Cell* 1:115–22 (1989)); and the CaMV 19S gene (Mogen et al., *Plant Cell* 2:1261–72 (1990)).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395–4405 (1988); Callis et al., *Genes Dev.* 1:1183–200 (1987)). Such intron enhancement of gene expression is typically greatest when placed near the 5' end of the transcription unit. Use of maize introns Adh1-S intron 1, 2, and 6, the Bronze-1 intron are known in the art. See generally, THE MAIZE HANDBOOK, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos et al., *J. Biol. Chem.* 264:4896–900 (1989)), such as the *Nicotiana plumbaginifolia* extension gene (De-Loose et al., *Gene* 99:95–100 (1991)); signal peptides which target proteins to the vacuole, such as the sweet potato sporamin gene (Matsuka et al., *Proc. Natl. Acad. Sci. USA* 88:834 (1991)) and the barley lectin gene (Wilkins et al., *Plant Cell,* 2:301–13 (1990)); signal peptides which cause proteins to be secreted, such as that of PRlb (Lind et al., *Plant Mol. Biol.* 18:47–53 (1992)) or the barley alpha amylase (BAA) (Rahmatullah et al., *Plant Mol. Biol* 12:119 (1989), and hereby incorporated by reference), or signal peptides which target proteins to the plastids such as that of rapeseed enoyl-Acp reductase (Verwaert et al., *Plant Mol. Biol.* 26:189–202 (1994)) are useful in the invention. The barley alpha amylase signal sequence fused to the ZMNAM polynucleotide is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., *Meth. Enzymol.* 153:253–77 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., *Gene* 61:1–11 (1987), and Berger et al., *Proc. Natl. Acad. Sci. USA,* 86:8402–6 (1989). Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al., *Gene* 22:229–35 (1983); Mosbach et al., *Nature* 302:543–5 (1983)). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman et al., METHODS IN YEAST GENETICS, Cold Spring Harbor Laboratory (1982) is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas ($7^{th}$ ed., 1992).

Appropriate vectors for expressing proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, *J. Embryol. Exp. Morphol.* 27:353–65 (1987)).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol.* 45:773–81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in DNA CLONING: A PRACTICAL APPROACH, vol. II, Glover, ed., IRL Press, Arlington, Va., pp. 213–38 (1985)).

In addition, the gene for ZMNAM placed in the appropriate plant expression vector can be used to transform plant cells. The enzyme can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert a ZMNAM polynucleotide into a plant host, including biological and physical plant transformation protocols. See, e.g., Miki et al., "Procedure for Introducing Foreign DNA into Plants," in METHODS IN PLANT MOLECULAR BIOLOGY AND BIOTECHNOLOGY, Glick and Thompson, eds., CRC Press, Inc., Boca Raton, pp. 67–88 (1993). The methods chosen vary with the host plant, and include chemical transfection methods such as calcium phosphate, microorganism-mediated gene transfer such as *Agrobacterium* (Horsch et al., *Science* 227:1229–31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in METHODS IN PLANT MOLECULAR BIOLOGY AND BIOTECHNOLOGY, supra, pp. 89–119.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, *Crit. Rev. Plant Sci.* 10:1 (1991). Descriptions of the *Agrobacterium* vector systems and methods for *Agrobacterium*-mediated gene transfer are provided in Gruber et al., supra; Miki et al., supra; and Moloney et al., *Plant Cell Reports* 8:238 (1989).

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, *Science* 244:174–81 (1989). Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. patent application Ser. No. 913,914, filed Oct. 1, 1986, as referenced in U.S. Pat. No. 5,262,306, issued Nov. 16, 1993; and Simpson et al., *Plant Mol. Biol.* 6: 403–15 (1986) (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A1 discloses a method for transforming monocots with *Agrobacterium* using the scutellum of immature embryos. Ishida et al. discuss a method for transforming maize by exposing immature embryos to *A. tumefaciens* (*Nature Biotechnology* 14:745–50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, *Theor. Appl. Genet.* 69:235–40 (1985); U.S. Pat. No. 4,658,082; Simpson, et al., supra; and U.S. patent application Ser. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei et al., *The Plant Journal* 6:271–82 (1994)). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford et al., *Part. Sci. Technol.* 5:27 (1987); Sanford, *Trends Biotech* 6:299 (1988); Sanford, *Physiol. Plant* 79:206 (1990); and Klein et al., *Biotechnology* 10:268 (1992)).

Another method for physical delivery of DNA to plants is sonication of target cells as described in Zang et al., *BioTechnology* 9:996 (1991). Alternatively, liposome or spheroplast fusions have been used to introduce expression vectors into plants. See, e.g., Deshayes et al., *EMBO J.* 4:2731 (1985); and Christou et al., *Proc. Natl. Acad. Sci. USA* 84:3962 (1987). Direct uptake of DNA into protoplasts using $CaCl_2$ precipitation, polyvinyl alcohol, or poly-L-ornithine has also been reported. See, e.g., Hain et al., *Mol. Gen. Genet.* 199:161 (1985); and Draper et al., *Plant Cell Physiol.* 23:451 (1982).

Electroporation of protoplasts and whole cells and tissues has also been described. See, e.g., Donn et al., in *Abstracts of the VIIth Int'l. Congress on Plant Cell and Tissue Culture IAPTC*, A2–38, p. 53 (1990); D'Halluin et al., *Plant Cell* 4:1495–505 (1992); and Spencer et al., *Plant Mol. Biol.* 24:51–61 (1994).

This invention can be better understood by reference to the following non-limiting examples. It will be appreciated by those skilled in the art that other embodiments of the invention may be practiced without departing from the spirit and the scope of the invention as herein disclosed and claimed.

EXAMPLE 1

Materials and Methods

Plant Material

Maize (*Zea mays* L.) inbred lines were either from the public collections or from the collection of Pioneer Hi-Bred International, Inc. (TABLE 1). Reciprocal crosses among the inbred lines were made in the field in 1998 to produce two sets of hybrids: B73/Mo17 and Mo17/B73; SSS1/NSS1 and NSS1/SSS1. Endosperm tissue was collected at 10, 14, and 21 days after pollination (DAP). Ears were collected from the field and endosperm tissue was dissected from the cob in the lab, frozen immediately in liquid $N_2$ and stored at −80° C. Materials for mRNA profiling were all collected in 1998. Due to the limited tissue remaining after mRNA profiling, additional tissue samples were collected in 2001 for allele-specific gene expression analyses.

TABLE 1

List of Inbreds[1] Used to Produce Hybrids of Reciprocal Crosses

| Inbred | Characteristics |
|---|---|
| B73 | Public US Iowa Stiff Stalk Synthetic (100%); Reid yellow dent (YD) type |
| Mo17 | Public US (YD) Lancaster Sure Crop (50%), Krug (50%) |
| SSS1 | Public line from Iowa Stiff Stalk Synthetic (100%). Reid yellow dent (YD) type. |
| NSS1 | Mid-maturity Non-Stiff Stalk (YD) type, not related to Mo17, Central US adaptation. |

[1]The inbred lines were crossed reciprocally to produce hybrids (B73/Mo17 and Mo17/B73) and (SSS1/NSS1 and NSS1/SSS1) and self crossed to re-produce the inbred lines.

RNA Isolation and Profiling

The endosperm was ground to fine powder in liquid $N_2$. Total RNA was extracted using TriPure reagent (Roche Molecular Biochemicals, Indianapolis, Ind.) according to the manufacturer's protocol. Poly-$A^+$ RNA was purified from total RNA using oligo (dT) magnetic beads (PerSeptive, Cambridge, Mass.) and quantified by fluorometry. Poly-$A^+$ RNA was then subjected to GeneCalling analysis as described in Shimkets et al., *Nat. Biotech.* 17:798–803 (1999)). Briefly, the following steps were involved in the GeneCalling process. Double-stranded cDNA was synthesized from the mRNA and digested with 48 different pairs of restriction enzymes (6-bp recognition sites). Adapters were ligated to the cDNA, which was then PCR amplified for 20 cycles using adapter-specific primers. After size fractionation on an electrophoresis gel, the fluorescamine (FAM)-labeled PCR products were quantified by a laser scanner. The fluorescent intensity from FAM-labeled cDNA fragments is proportional to the abundance of the corresponding mRNA expressed in the given tissue.

The same 48 pairs of PCR primers were used for all the samples in this study, which covers 80–85% of the expressed genes represented in the mRNA pool from the tissue analyzed (Shimkets et al., supra). For each primer pair, three independent PCRs were made from an individual mRNA sample. A composite trace is calculated based on the average peak height and variance of the three PCR reactions from each sample (Shimkets et al., supra). One mRNA sample from each genotype was analyzed (three PCR reactions), except for one genotype in which three experimental replicates were profiled (nine PCR reactions).

Data Processing

The mRNA profile data was obtained for hybrids and inbred parents from 10, 14 and 21 DAP endosperm. The profile of each sample consisted of approximately 22,000 expressed cDNA fragments resulting from 48 PCR primer pairs. An algorithm was first designed to test the presence of significant variations between two samples due to systematic error in the mRNA profiling process. The expression level difference of each cDNA fragment across all samples was calculated and no systematic error was found. The data was normalized based on the assumption that the majority of the transcripts from a given tissue type remain unchanged among genotypes. Since the comparisons were to be made within the same developmental stages of different genotypes, the data was normalized across genotypes for each developmental stage. The average number of expressed cDNA fragments resulting from one restriction enzyme pair was 450. Normalization at each developmental stage was therefore carried out with approximately 324,000 expression data points from each developmental stage. Comparisons between experimental replicates of the same genotype indicated that there was little scaling variation after the normalization. The normalized data was stored in an ORACLE8 database, where various data analyses were performed by using Standard Query Language (SQL).

Selection of Differentially Expressed Genes

Two different selection criteria were used to select cDNA fragments. One method was based on the present/absent criterion where cDNA fragments were present in one parent but absent or at the background level in the other. The second selection was based on a 2-fold cut-off criterion in which case cDNA fragments were present in both parents but different in at least 2-fold in the level of expression.

Profiles of four endosperm genotypes are compared in each hybrid set: inbred parents AA/A and BB/B, and reciprocal hybrids AA/B and BB/A. The present/absent selection criterion was applied to the cDNA fragments that are present in AA/A but absent in BB/B, for instance. Such individual cDNAs representing the A allele are selected if they are present through maternal transmission in hybrid AA/B, but not in the reciprocal hybrid BB/A where A is paternally transmitted. The same strategy was used to select cDNA fragments that represent the paternal allele.

The 2-fold cut-off selection is principally the same as the present/absent selection except that a minimum of 2-fold difference in the expression level is used in place of the present/absent criterion. The first selection was for those cDNAs that have a minimum of 2-fold difference in expression level between the parents AA/A and BB/B. cDNAs were further selected that have the same expression level in the hybrid (e.g. AA/B) as in the maternal parent (AA/A), but are different by at least 2-fold from the reciprocal hybrid BB/A where A is paternal allele.

Allele-Specific Gene Expression Analysis

Total RNA was extracted and prepared using the same protocols as used for GeneCalling. The total RNA was then treated with Dnase I (Invitrogen, Carlsbad, Calif.). First-strand cDNA was synthesized using SuperScriptII (Invitrogen, Carlsbad, Calif.). Gene-specific primers were used to obtain the cDNA from each inbred parent by RT-PCR with Pwo polymerase (Roche, Indianapolis, Ind.). The PCR products were then sequenced to identify allele sequence polymorphisms between the inbred lines that would allow separation of the two parental alleles on the WAVE dHPLC system (Transgenomic, Omaha, Nebr.). Primers were designed in consensus regions between the parental alleles to eliminate amplification preference to either allele and to optimize the amplicon for analysis on the WAVE. Thirty-cycle PCR was performed with the cDNA of each inbred and hybrid. Thirty-cycle PCR was elected because at lower cycle numbers both alleles were not always detected. The PCR products were then subjected to the WAVE dHPLC system for separation.

If a size difference of greater than 1% was present between the two parental alleles for a given gene, a size-based separation was performed under non-denaturing (50° C.) conditions on the WAVE. If the PCR products from the two parental alleles are the same size and contain single nucleotide polymorphisms (SNPs), the samples were run under partially denaturing (mutation detection) conditions to allow separation of the homoduplex peaks in the hybrid samples. When using partially denaturing conditions, the PCR reactions were heated to 95° C. for 5 min and allowed to cool slowly to 25° C. over a 45-min period in order to allow re-annealing prior to running the samples on the WAVE. The optimal temperature for mutation detection must be determined empirically for each gene sequence. Chromatogram traces for each PCR were generated by UV detection and peak areas were calculated by the WAVE-MAKER software (Transgenomic, Omaha, Nebr.).

Tissue Specific Expression Analysis of the No Apical Meristem (ZMNAM) Gene

Endosperm and embryo tissues of 16 DAP kernels and ovule tissue from B73 were carefully dissected under a microscope to ensure no cross-contamination of tissue. The root, stalk, leaf, immature ear and tassel tissues were collected from B73 at the V12 stage. The RNA from each tissue was purified and treated with Dnase. Sample size used was 1 µg of RNA from each tissue for RT-PCR. Thirty-cycle RT-PCR (protocol as described above) was performed using ZMNAM gene-specific primers with cDNA from each tissue type. RT-PCR of the α-tubulin gene was performed using the same cDNA from each tissue as a control of cDNA quality and PCR robustness. Each PCR sample was then run on a gel consisting of 1% Seakem LE agarose (BMA, Rockland, Me., U.S.A.), 1×TBE for 90 min at 70 volts and stained with ethidium bromide. Molecular weight marker VIII (Roche, Indianapolis, Ind., U.S.A.) was used to confirm the size of the amplified genes.

H/P Ratio Calculation

In order to measure the F1 hybrid expression level in relation to the parental levels for a corresponding cDNA fragment, the metric of Hybrid/Parent (H/P) ratio was developed. Because of the nature of the endosperm the maternal parent contributes two doses and the paternal parent contributes one dose to the genetic constitution. Additive allelic expression in the hybrid would give an average expression level of Ave=(2 $P_{female}$+1$P_{male}$)/3. Therefore, for each cDNA fragment that is different between the parents, the deviation of the actual hybrid expression level from the average of the parents, as H=F1−Ave was first calculated and then the deviation of one parent (male) from the average as P=$P_{male}$−Ave was calculated. The ratio of the H/P is used to measure the hybrid expression level in relation to the average of parental level. If the hybrid expression level is equal to the average expression level, then H=F1−Ave=0, which results in H/P=0. Therefore, a zero value of the H/P ratio indicates that the level of expression in the hybrid is the same as the average of the parents and fits the predicted additive allelic expression. If the hybrid expression deviates from the average expression level and is biased towards the male parent's level, then the values H=F1−Ave and P=$P_{male}$−Ave, would both be negative or both positive, resulting in H/P>0. Likewise, H/P<0 will be obtained if the hybrid expression is biased towards the female parent's level, where the values H=F1−Ave and P=$P_{male}$−Ave, would be opposite in sign, that is, one is negative and the other is positive. While the sign of the H/P ratio indicates the direction of the deviation, maternal or paternal, the absolute value of the H/P ratio indicates the degree of the deviation.

Results

Parent-Specific Gene Expression in Hybrid Endosperm

With GeneCalling technology, cDNA fragment differences between genotypes could be attributed to two sources: (1) differential mRNA expression and (2) allelic sequence polymorphism (Shimkets et al., supra; Bruce et al., *The Plant Cell* 12:65–79 (2000)). Reciprocal hybrids have the same genetic constitution and therefore allow the identification of cDNA fragments corresponding to differentially expressed genes due to parent-specific regulation.

If a gene is expressed independent of its parent-of-origin, the parental alleles would be expected to express equally or in allele dosage manner in the hybrid regardless of the crossing direction. On the other hand, if a gene is affected by parental source, the allelic expression would vary depending upon maternal or paternal transmission. By comparing reciprocal F1 hybrids and their parents, cDNA fragments corresponding to a gene that is differentially expressed when transmitted maternally or paternally, either present/absent or level difference, were identified.

Allele-Specific Analysis of Gene Expression

Figure 3:
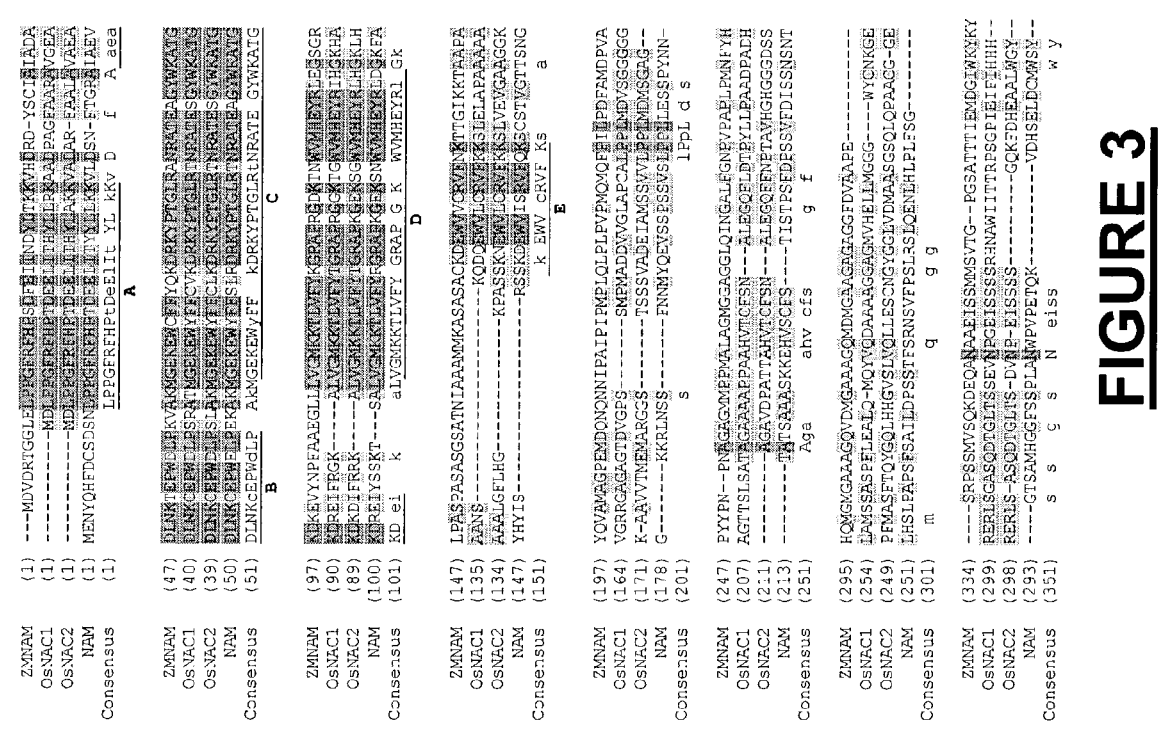

Three cDNA fragments that exhibited parent-specific expression to a different extent in the GeneCalling profiles were isolated and sequenced for further verification and characterization. Based on the sequence homology of the isolated cDNAs with genes in databases, it was determined that these cDNA fragments correspond to a maize homolog of No-Apical Meristem (ZMNAM) (TABLES 2 and 3). NAM was originally described in Petunia and was shown to be required for pattern formation in embryos and flowers. Petunia embryos carrying the NAM mutation failed to develop a shoot apical meristem (Souer et al., supra). This gene appears to be a member of a large gene family that are suggested to be transcriptional factors important to plant development (Souer et al., supra; Kikuchi et al., supra). The ZMNAM protein belongs to a family of NAM transcription factors as shown by the alignment of the amino acid sequence of ZMNAM with Petunia NAM and two rice homologues OsNAC1 and OsNAC2 (FIG. 3). The NAC domains are highly conserved among the NAM/NAC family members (Kikuchi et al., 2000).

TABLE 2

Sequences of cDNA Fragments Corresponding to ZMNAM cgzmi0a0309.2:

(SEQ ID NO:1)
GGTACCATCATGCCCCGGATTACTAAGACCAAACGACACACACATATACC

ACACATGCAATGATACAATGCATGTATATACTAGCACATGCATGCACACA

TATCTTACCGACTAGTTATTGCAGAAATATAGGAACCATGCAAATTTTCA

CAAAATGCAATGCAGATATAGTAGATATAACATGCATATTCATGCATTTG

TCTCCAAACTCCATATCCACTTTTTCAGTACTTGTACTTCCATATGCCAT

CCATC cgzmi0a0319.2:

(SEQ ID NO:2)
GGTACCATCATGCCCCGGATTACTAAGACCAAACGACACACACATATACC

ACACATGCAATGATACAATGCATGTATATACTAGCACATGCATGCACACA

TATCTTACCGACTAGTTATTGCAGAAATATAGGAACCATGCAAATTTTCA

CAAAATGCAATGCAGATATAGTAGATATAACATGCATATTCATGCGAATT

TABLE 2-continued

Sequences of cDNA Fragments Corresponding to ZMNAM

CATGCATTTGTCTCCAAACTCCATTTTCACTTTTTCAGTACTTGTACTTC

CATAT cgzmd0p0125.6:

(SEQ ID NO:3)
RGATCTCGTCGATGATGTCTGTGACCGGCCCAGGGTCCGCGACCACCACC

ATAGAGATGGATGGCATATGGAAGTACAAGTACTGAAAAAGTGAAAATGG

AGTTTGGAGACAAATGCATGAATTY p0029.cdsaf13r.fis1

(SEQ ID NO:4)
CAAGAAGACGGCTGCGCCGGCATACCAGGTGGCCATGGCCGGTCCTGAGA

TGGATCAGAATCAGAACAACATTCCGGCCATCCCCATCCCCATGCCGCTG

CAGCTGCCACTGCCCGTGCCCATGCAGATGCAATTTCCCATCCTGCCAGA

TTTTGCCATGGACCCGGTGGCCCCCTACTACCCCAACCCGAATGCCGGCG

CGGGGATGATGCCGCCTATGGCATTGGCAGGTATGGGTGGCGCCGGCGGG

CTCCAGATCAACGGCGCTCTGTTCGGCAATCCGGTGCCCGCGCCGCTGCC

GATGAACTTCTACCACCACCAGATGGGCATGGGGGCAGCAGCTGGCCAGG

TGGACATGGGGGCAGCGGCTGGCCAGATGGACATGGGAGCAGCTGGCGCT

GGCGCTGGCGGCTTCGACGTTGCAGCGCCGGAGAGTAGGCCGTCCTCGAT

GGTGTCACAGAAGGACGAACAGGCTAATGCCGCCGAGATCTCGTCGATGA

TGTCTGTGACCGGCCCAGGGTCCGCGACCACCACCATAGAGATGGATGGC

ATATGGAAGTACAAGTACTGAAAAAGTGGATATGGAGTTTGGAGACAAAT

GCATGAATATGCATGTTATATCTACTATATCTGCATTGCATTTTGTGAAA

ATTTGCATGGTTCCTATATTTCTGCAATAACTAGTCGGTAAGATATGTGT

GCATGCATGTGCTAGTATATACATGCATTGTATCATTGCATGTGTGGTAT

ATGTGTGTCGTTTGGTCTTAGTAATCCGGGCATGATGGTACCCATAC

CTGGATTTACATCTGCTTGGTCGTGCTGATGTTGTGTTGTAATTTGTAAA

AAGCAGATTGAAGTTCGGTACAGTATATTATCGTGAACCTATAAAAAAAA

AAAAAAAAAAAAAAAAAAAAAAAAA

TABLE 3

| Putative ID | Score | E | EST |
|---|---|---|---|
| BLAST Results with SEQ ID NO:1 | | | |
| gi\|862343\|gb\|AAA 68426.1\| (L10908) Gcap1 gene product [Mus musculus] >gi\|1092097\|prf\|\|2 022314A granule cell marker protein [Mus musculus] E = 3.0 [5'(9),3'(2) | 1824 | 0 | p0029.cdsaf13ra |

TABLE 3-continued

| Putative ID | Score | E | EST |
|---|---|---|---|
| PCL109136(11) p0029.cdsaf13ra] gi\|2275201\|gb\|AA B63823.1\| (AC002337) unknown protein [Arabidopsis thaliana] E = 0.18 [5'(8),3'(2) | 194 | 8E-49 | p0066.cgrah36ra |
| PCL122057(11) p0066.cgrah36ra] gi\|6223650\|gb\|AA F05864.1\|AC0116 98_15 (AC011698) NAM-like protein (no apical meristem) [Arabisopsis thaliana] E = 2e-70 [5'(22),3'(0) | 111 | 1E-23 | p0083.clddz12r |
| PCL086981(56) p0083.clddz12r] no significant hits (pLog(P) > 4) [5'(1),3'(0) PCL096720(1) cen3n.pk0080.d1] | 48 | 0.0001 | CEN3N.PK0080.D 1 |
| BLAST RESULTS FROM SEQ ID NO:4 | | | |
| gb\|AAK11704.1\|A F345525_1 (AF345525) Orf1 [TT virus]. | 363 | 3-153 | p0029.cdsaf13r |
| ref\|NP_197328.1\| NAM (no apical meristem)-like protein [Arabidopsis thaliana]. | 169 | 1.00E-41 | p0113.cieah48r |
| gb\|AAK11704.1\|A F345525_1 (AF345525) Orf1 [TT virus]. | 149 | 7.00E-36 | p0029.cdsaf13r |
| ref\|NP_196385.1\| NAM (no apical meristem)-like protein [Arabidopsis thaliana]. | 45 | 4.00E-09 | cen3n.pk0191.a |

Expression pattern of this gene in hybrids was verified by using the WAVE dHPLC system, which allows allele-specific gene expression analysis when a resolvable allele sequence polymorphism is present between the alleles. Both parental alleles can be visualized simultaneously and the relative expression level of the parental alleles in the hybrids was measured. The gene in two hybrids of different genetic backgrounds was examined if resolvable allelic sequence polymorphism could be found. Tissue samples from different years were used for the allele-specific gene expression analysis. Tissue samples from both years for one developmental stage (14 DAP) were also included as controls and indeed consistent results were observed between the years. The expression patterns of the gene in GeneCalling for one hybrid is shown in FIG. 1. The allele-specific expression results from the WAVE (FIG. 2) were consistent with that observed in GeneCalling. Since gene-specific primers and 30 cycle PCR were used in the RT-PCR for dHPLC analysis as compared to non-gene-specific primers and 20 cycle PCR used in GeneCalling, WAVE analysis is more sensitive than GeneCalling profiling and the increased PCR cycle number in WAVE may therefore actually underestimate the expression differences between the alleles.

ZMNAM Expression Profile During Endosperm Development

Figure 5:
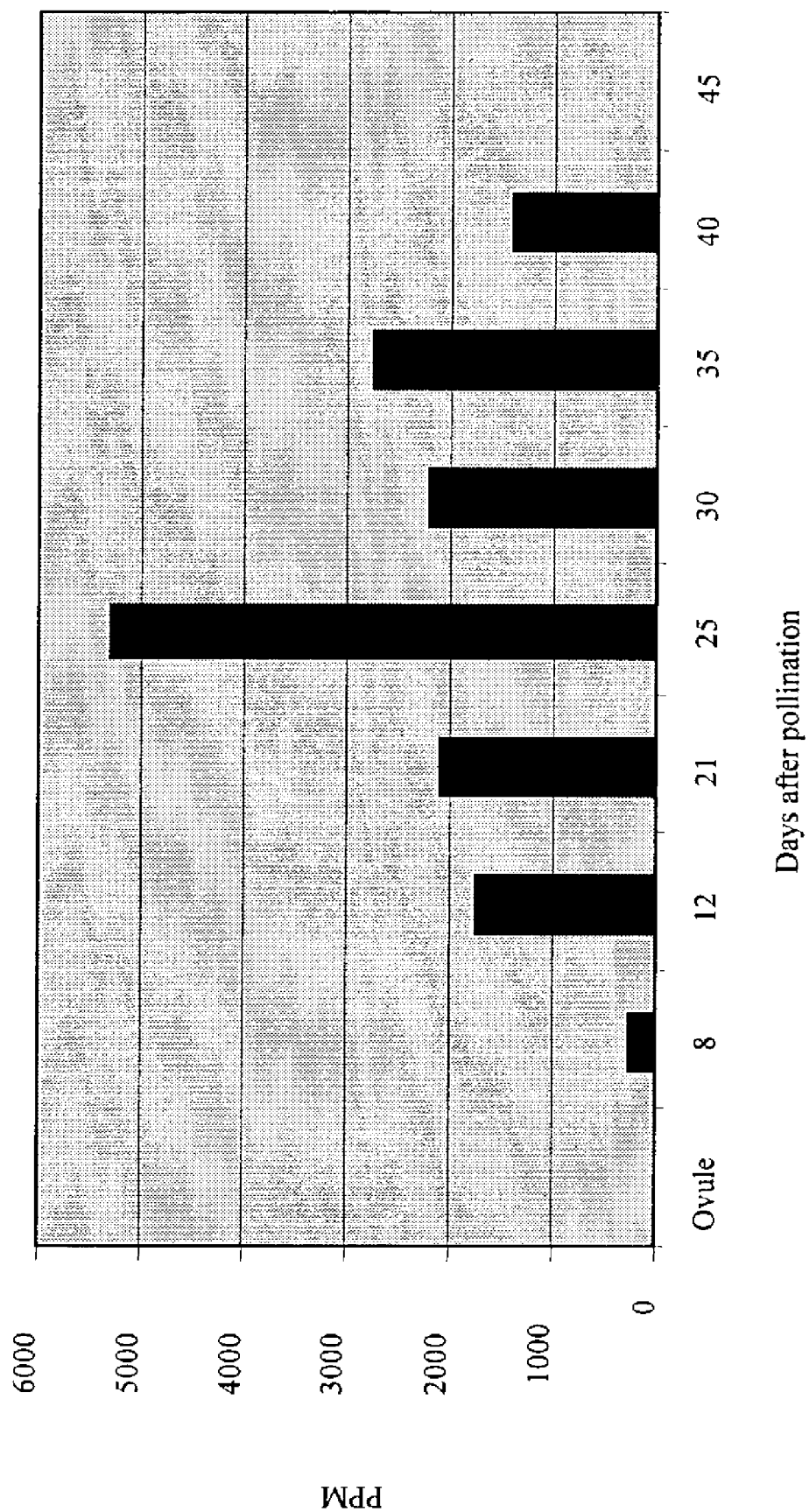
FIG. 5 details the expression profile of ZMNAM as generated by MPSS, during kernel development. The y-axis represents the frequency of the 17-mer tags as parts per million sequenced and therefore the level of expression. The x-axis is the stages of the kernel development: ovule (0), 8, 12, 21, 25, 30, 35, 40 and 45 DAP. The ZMNAM expression during kernel development was analyzed using the Massively Parallel Signature Sequencing (MPSS) (Brenner et al., 2000a, 2000b). With the MPSS technique, each cDNA is attached to the surface of a unique microbead. A highly expressed mRNA is represented on a proportionately large number of microbeads. Signature sequences of 17 nucleotides are then obtained from these microbeads by iterative cycles of restriction with a type IIs endonuclease, adaptor ligation, and hybridization with encoded probes. The number of signatures in each library ranged from $1.2 \times 10^6$ to $2.2 \times 10^6$. For each tissue, the data were averaged from one or more libraries. Tissue was from B73 inbred. The technique provides an unprecedented depth and sensitivity of mRNA detection, including very low expressed messages. The level of expression (parts per million, PPM) of a gene is determined by the abundance of its signature in the total pool. The ZMNAM gene was expressed throughout endosperm development, peaking at 25 DAP and was not detected in the ovule. These results also indicate that the ZMNAM gene was expressed only after fertilization occurs.

The ZMNAM expression during kernel development was analyzed using the MPSS (FIG. 5). The technique provides an unprecedented depth and sensitivity of mRNA detection, including very low expressed messages. The level of expression (parts per million, PPM) of a gene is determined by the abundance of its signature in the total pool. The ZMNAM gene was expressed throughout endosperm development, peaking at 25 DAP and was not detected in the ovule. These results also indicate that the ZMNAM gene was expressed only after fertilization occurs.

Figure 2:
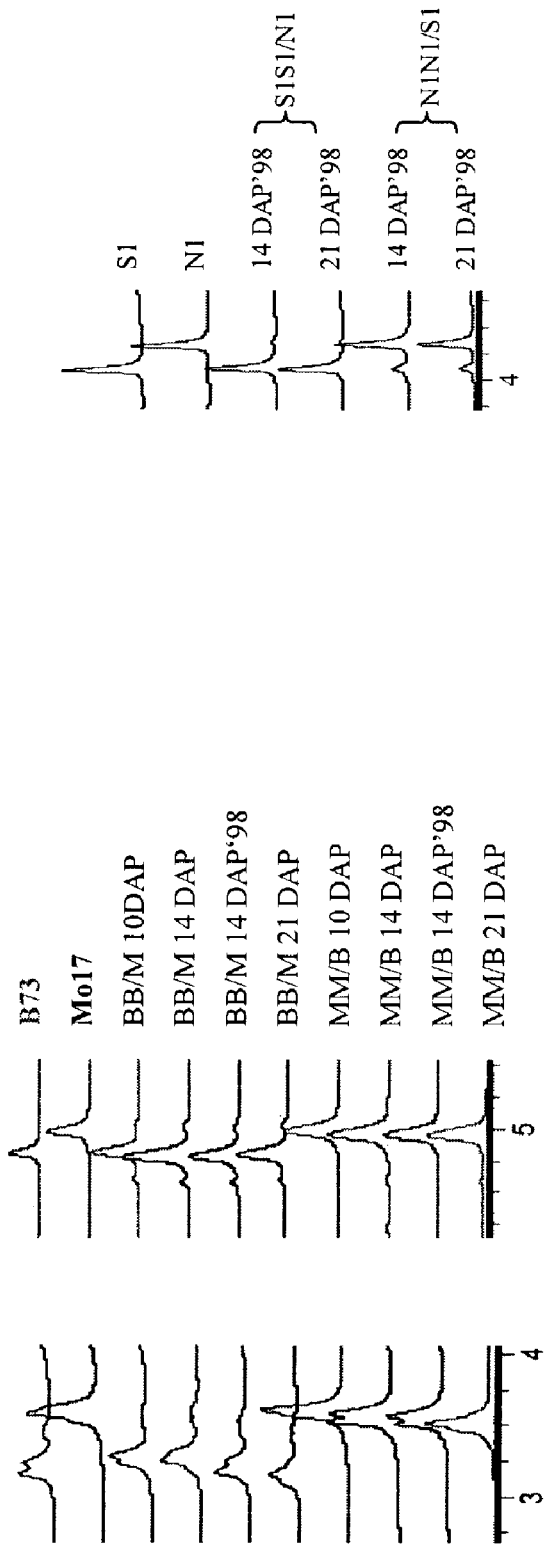
FIG. 2 shows the imprinting and tissue specific expression results of ZMNAM gene from the WAVE dHPLC system (Transgenomic, Omaha, Nebr., U.S.A.) (B=B73; M=Mo17; S1=SSS1; N1=NSS1). In the hybrid name, the first genotype denotes the female parent and second genotype denotes the male parent. Allele-specific expression results are shown for both members and single gene member, respectively, for hybrids 1 (the far left two panels). On the right is the single gene member for hybrid 2. Parental alleles are expressed highly when maternally transmitted. The paternally transmitted alleles are either completely or near completely silenced, indicating the parent-of-origin effect.
Figure 2:
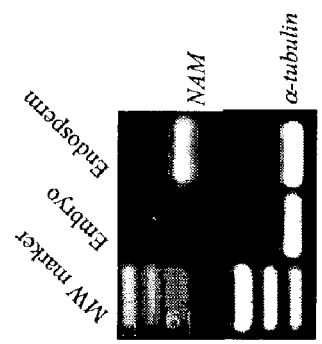
Figure 4:
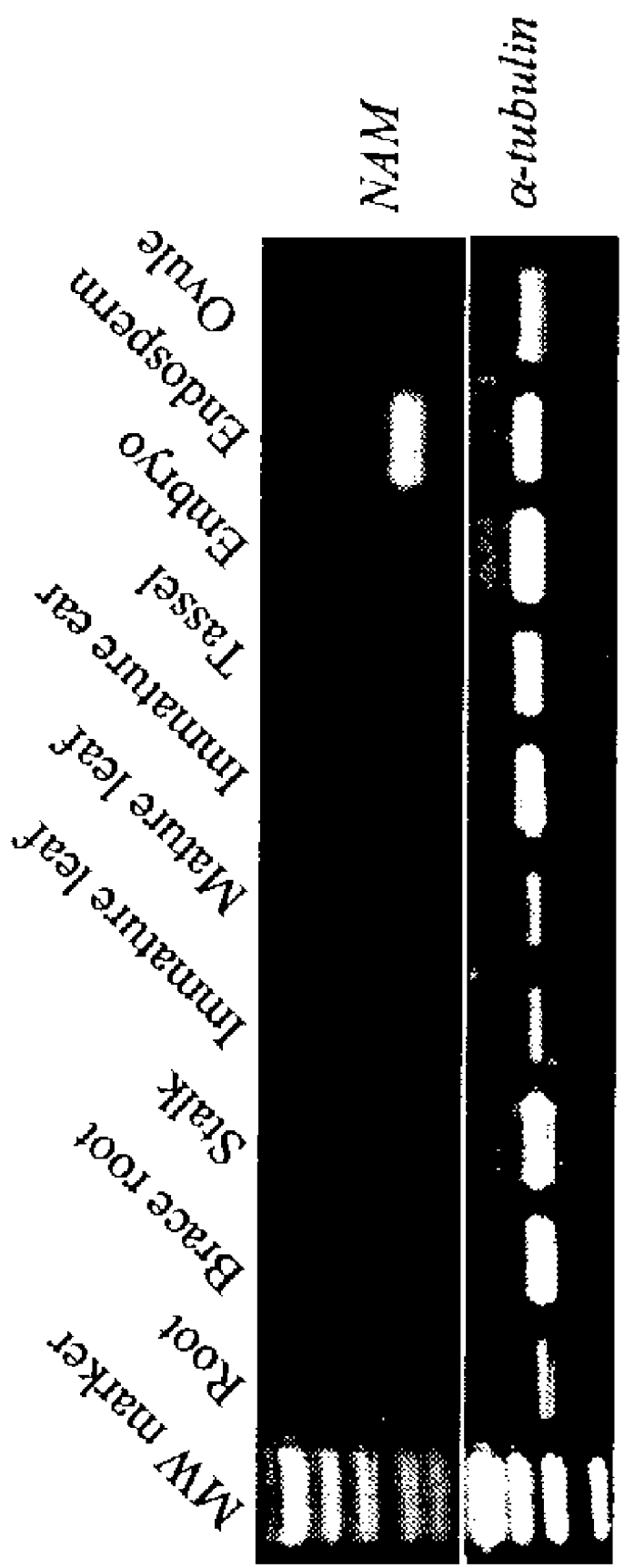
FIG. 4 shows tissue-specific expression using RT-PCR analysis of maize RNA. In the tissue-specific expression analysis, equal amounts of total RNA from the root, stalk, leaf, immature ear, tassel, endosperm, embryo and ovule was used for RT-PCR. All vegetative tissues were collected from B73 at V12 stage. Endosperm and embryo tissues were collected at 16 DAP and ovules were collected before fertilization. Thirty-cycle RT-PCR was performed using the ZMNAM gene-specific primers. α-tubulin was used as a control for cDNA quality. No expression is detected in the ovule tissue, indicating the gene is not expressed prior to fertilization.

The pattern of expression confirmed is the imprinted expression pattern of the ZMNAM homologue. The ratio of maternal allele: paternal allele expression level deviated from 2:1 (FIG. 2 and TABLE 4). While the maternally transmitted alleles were expressed, the paternally transmitted alleles were nearly silenced throughout the developmental stages analyzed. The paternally transmitted alleles were expressed at a very low level that could be barely detected or visualized with 30-cycle RT-PCR and could not be detected with 20-cycle RT-PCR. The imprinted expression of the ZMNAM gene was found in both hybrids examined of different genetic backgrounds, suggesting lack of allele specificity. The imprinting expression pattern of this gene resembles the imprinted alleles of the R gene, a transcription factor in the anthocyanin pathway. When R is used as the female parent, the aleurone is solidly colored, when used as the male parent R is partially silenced and gives rise to mottled aleurone pigmentation (Kermicle, supra). The exact role of the ZMNAM gene being imprinted remains to be determined. The biological significance of gene imprinting in endosperm is not well understood. The known imprinted genes affecting endosperm development reported so far are MEA, FIS2 and FIE in *Arabidopsis* (Grossniklaus et al., supra; Luo et al., supra; Chaudhury et al., *Ann. Rev. Cell. Dev. Biol.* 17:677–99 (2001)). Other imprinted genes characterized in plants were not essential to seed development (Kermicle, supra; Kermicle and Alleman, *Development* Suppl.:9–14 (1990); Chaudhuri and Messing, supra; Lund et al., *Mol. Gen. Genet* 246:716–22 (1995); Vielle-Calzada et al., *Genes & Dev.* 13:2971–82 (1999)). Members of the NAM family are shown to play important roles in plant development (Souer et al., supra; Kikuchi et al., supra). The expression of the ZMNAM gene appeared to be highly specific to endosperm tissue based on electronic Northern analysis and BLAST search in the public EST database. The results from RT-PCR analysis also indicate that the expression of the ZMNAM gene is endosperm-specific (FIG. 4). It has been suggested that the hypothetical ancestral representatives of gene families and their broad expression pattern may have been co-opted for specialized functions, for instance, members of the MADS-box family are found expressed in the endosperm and developing male and female gametes in *Arabidopsis* (Alvarex-Buylla et al., *The Plant J.* 24:457–66 (2000); Lohe and Chaudhury, *Curr. Opin. Plant Biol.* 5:19–25 (2002)). Similar results were reported with the family of WD-repeat proteins in maize. A member of the ZmRbAp (retinoblastoma-associated protein) genes is expressed during endosperm development and is also expressed in the shoot apical meristem and leaf primordial of the embryo (Rossi et al., *Mol. Gen. Genomics* 265:576–84 (2001)). In this study a new imprinted gene, ZMNAM, was discovered which had not previously been described in maize. Results indicated that ZMNAM was regulated by gene-specific imprinting in the genotypes examined.

ZMNAM is the second gene that has been characterized in maize as exhibiting gene-specific imprinting, the first one being FIE. Furthermore, ZMNAM was expressed exclusively in the endosperm, throughout endosperm development and peaked at 25 DAP. The endosperm specific expression of ZMNAM is consistent with the notion that imprinted genes are primarily expressed in the endosperm (Alleman and Doctor, 2000; Haig and Westoby, 1989). ZMNAM is a member of a large gene family that is suggested to be transcriptional factors important to plant development (Kikuchi et al., 2000; Souer et al., 1996). The highly conserved domains between ZMNAM, rice NAC and Petunia NAM proteins suggest that the ZMNAM gene may function as a transcription factor (see FIG. 3). The gene-specific imprinting of ZMNAM implicates its important role as a putative transcription factor in endosperm development.

TABLE 4

Ratio of Paternal and Maternal Allele Expression in Relation to Dosage in Endosperm[1]

| Endosperm Genotype | Mean (M/P) | SE | p |
|---|---|---|---|
| BB/M[2] 10 DAP | 8.76 | 0.50 | 0.002 |
| BB/M 14 DAP | 8.43 | 0.80 | 0.005 |
| BB/M 14 DAP (98) | 8.43 | 0.19 | 0.000 |
| BB/M 21 DAP | 9.97 | 0.49 | 0.001 |
| MM/B 10 DAP | 186.48 | 17.27 | 0.003 |
| MM/B 14 DAP | 142.40 | 7.30 | 0.001 |
| MM/B 14 DAP (98) | 155.78 | 1.77 | 0.000 |
| MM/B 21 DAP | 90.29 | 8.40 | 0.003 |
| S1S1/N1 14 DAP | 40.49 | 4.12 | 0.004 |
| S1S1/N1 21 DAP | 53.65 | 1.55 | 0.000 |
| N1N1/S1 14 DAP | 3.36 | 0.02 | 0.000 |
| N1N1/S1 21 DAP | 4.27 | 0.38 | 0.008 |

[1]Ratio of the maternal to paternal allele (M/P) was calculated using allele peak areas and compared with predicted ratio of 2 maternal: 1 paternal according to allelic dosage gene expression. The average ratio (mean) and the standard error (SE) based on three replicates of the WAVE dHPLC data are shown. All samples were collected in 2001 except those marked with "98," which were sampled in 1998.
[2]B = B73; M = Mo17. S1 = SS1, N1 = NSS1.

Genomic Sequence of ZMNAM Gene and Two CpG Islands

To determine the genomic structure of the ZMNAM gene, a genomic copy was sequenced from BAC (bacterial artificial chromosome) clone, identified by hybridization of BAC libraries with the ZMNAM specific probe from the 3' UTR (SEQ ID NO: 1). Genomic fragments of 3.8-kb were sequenced (SEQ ID NO: 5). This corresponds to the second exon and 3' UTR of the ZMNAM gene. Comparison of the full-length cDNA of the ZMNAM with the rice genomic sequence (rice chromosome 1, BAC clone: B 1109A06) suggests that in monocots this gene is composed of two exons and one intron.

The ZMNAM gene is imprinted in the maize endosperm. Imprinting is a developmental phenomenon wherein a gene in a gamete or zygote is modified such that preferential expression of a single parental allele occurs in the offspring. It has been theorized that "CpG islands" present within the gene are subject to methylation, which causes repression of one allele (Stoger et al. (1993) *Cell* 73:61–71). CpG islands are defined as sequences of 200 or more base pairs with a GC content greater than 0.5 and an observed-to-expected CpG dinucleotide content greater than 0.6 (Gardiner-Garden and Frommer (1987) *J. Mol. Biol.* 196:261–282). The two island rule was postulated for imprinted genes in mammals (Onyango et al. (2000) *Genome Research* 10:1697–1710). According to this rule two or more CpG islands are characteristic features of the imprinted genes. Analysis of the genomic structure of the ZMNAM reveals two CpG islands. The first CpG island is located in the 5' segment of the cDNA (SEQ ID NO: 8). The second CpG island is located downstream of 3' UTR (SEQ ID NO: 5). Thus the ZMNAM gene follows the two-island rule. Previously an imprinted gene (Fie1) was identified in the maize endosperm with two CpG islands (Danilevskaya et al., (2003) *Plant Cell*, 15:425–438). Discovery of two CpG islands within the two-island rule for mammals imprinted genes in plants agree with the two-island rule for mammals imprinted genes. Since the ZMNAM is expressed specific to the endosperm tissue and at a high level throughout endosperm development, the promoter of this gene can be used for engineering a gene that targets very specific expression in the endosperm tissue. Also, the gene specific imprinting nature of the ZMNAM gene can be used to engineer or modify a gene expression such that it is expressed only when transmitted from the maternal parent.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention

What is claimed is:

1. An isolated polynucleotide encoding a maize non-apical meristem nucleic acid comprising a polynucleotide selected from:
   a) a polynucleotide comprising SEQ ID NO:7;
   b) a polynucleotide having at least 95% sequence identity to SEQ ID NO:7;
   c) a polynucleotide encoding a polypeptide comprising SEQ ID NO:6; and
   d) a polynucleotide fully complementary to a polynucleotide of (a) through (c).

2. A recombinant expression cassette comprising a polynucleotide encoding a maize non-apical meristem nucleic acid selected from the group consisting of:
   a) a polynucleotide comprising SEQ ID NO:7;
   b) a polynucleotide having at least 95% sequence identity to SEQ ID NO:7;
   c) a polynucleotide encoding a polypeptide comprising SEQ ID NO:6; and d) a polynucleotide fully complementary to a polynucleotide of (a) through (c).

3. A vector comprising a recombinant expression cassette comprising a polynucleotide encoding a maize non-apical meristem nucleic acid selected from the group consisting of:
   a) a polynucleotide comprising SEQ ID NO:7;
   b) a polynucleotide having at least 95% sequence identity to SEQ ID NO:7;
   c) a polynucleotide encoding a polypeptide comprising SEQ ID NO:6; and
   d) a polynucleotide fully complementary to a polynucleotide of (a) through (c).

4. A host cell comprising a recombinant expression cassette comprising a polynucleotide encoding a maize non-apical meristem nucleic acid selected from the group consisting of:
   a) a polynucleotide comprising SEQ ID NO:7;
   b) a polynucleotide having at least 95% sequence identity to SEQ ID NO:7;
   c) a polynucleotide encoding a polypeptide comprising SEQ ID NO:6; and
   d) a polynucleotide fully complementary to a polynucleotide of (a) through (c).

5. The host cell of claim 4 wherein the cell is a plant cell.

6. The host cell of claim 5 wherein the cell is selected from the group consisting of maize, sorghum, wheat, tomato, soybean, alfalfa, sunflower, canola, cotton, and rice.

7. A transformed plant comprising a polynucleotide encoding a maize non-apical meristem nucleic acid selected from the group consisting of:
   a) a polynucleotide comprising SEQ ID NO:7;
   b) a polynucleotide having at least 95% sequence identity to SEQ ID NO:7;
   c) a polynucleotide encoding a polypeptide comprising SEQ ID NO:6; and
   d) a polynucleotide fully complementary to a polynucleotide of (a) through (c).

8. A transgenic seed from the transformed plant of claim 7, comprising a polynucleotide encoding a maize non-apical meristem nucleic acid selected from the group consisting of:
   a) a polynucleotide comprising SEQ ID NO:7;
   b) a polynucleotide having at least 95% sequence identity to SEQ ID NO:7;
   c) a polynucleotide encoding a polypeptide comprising SEQ ID NO:6; and
   d) a polynucleotide fully complementary to a polynucleotide of (a) through (c).

* * * * *

SEQUENCE LISTING

```
<160> NUMBER OF SEQ ID NOS: 10
<210> SEQ ID NO 1
<211> LENGTH: 255
<212> TYPE: DNA
<213> ORGANISM: Zea mays

<400> SEQUENCE: 1
ggtaccatca tgccccggat tactaagacc aaacgacaca cacatatacc acacatgcaa      60
tgatacaatg catgtatata ctagcacatg catgcacaca tatcttaccg actagttatt     120
gcagaaatat aggaaccatg caaattttca caaaatgcaa tgcagatata gtagatataa     180
catgcatatt catgcatttg tctccaaact ccatatccac tttttcagta cttgtacttc     240
catatgccat ccatc                                                     255

<210> SEQ ID NO 2
<211> LENGTH: 255
<212> TYPE: DNA
<213> ORGANISM: Zea mays

<400> SEQUENCE: 2
ggtaccatca tgccccggat tactaagacc aaacgacaca cacatatacc acacatgcaa      60
tgatacaatg catgtatata ctagcacatg catgcacaca tatcttaccg actagttatt     120
gcagaaatat aggaaccatg caaattttca caaaatgcaa tgcagatata gtagatataa     180
catgcatatt catgcgaatt catgcatttg tctccaaact ccattttcac tttttcagta     240
cttgtacttc catat                                                     255

<210> SEQ ID NO 3
<211> LENGTH: 125
<212> TYPE: DNA
<213> ORGANISM: Zea mays

<400> SEQUENCE: 3
rgatctcgtc gatgatgtct gtgaccggcc cagggtccgc gaccaccacc atagagatgg      60
atggcatatg gaagtacaag tactgaaaaa gtgaaaatgg agtttggaga caaatgcatg     120 aatty                                                                125

<210> SEQ ID NO 4
<211> LENGTH: 926
<212> TYPE: DNA
```

```
<213> ORGANISM: Zea mays

<400> SEQUENCE: 4
caagaagacg gctgcgccgg cataccaggt ggccatggcc ggtcctgaga tggatcagaa      60
tcagaacaac attccggcca tccccatccc catgccgctg cagctgccac tgcccgtgcc     120
catgcagatg caatttccca tcctgccaga ttttgccatg gacccggtgg ccccctacta     180
ccccaacccg aatgccggcg cggggatgat gccgcctatg gcattggcag gtatgggtgg     240
cgccggcggg ctccagatca acggcgctct gttcggcaat ccggtgcccg cgccgctgcc     300
gatgaacttc taccaccacc agatgggcat ggggcagca gctggccagg tggacatggg     360
ggcagcggct ggccagatgg acatgggagc agctggcgct ggcgctggcg gcttcgacgt     420
tgcagcgccg gagagtaggc cgtcctcgat ggtgtcacag aaggacgaac aggctaatgc     480
cgccgagatc tcgtcgatga tgtctgtgac cggcccaggg tccgcgacca ccaccataga     540
gatggatggc atatggaagt acaagtactg aaaaagtgga tatggagttt ggagacaaat     600
gcatgaatat gcatgttata tctactatat ctgcattgca ttttgtgaaa atttgcatgg     660
ttcctatatt tctgcaataa ctagtcggta agatatgtgt gcatgcatgt gctagtatat     720
acatgcattg tatcattgca tgtgtggtat atgtgtgtgt cgtttggtct tagtaatccg     780
gggcatgatg gtaccatac ctggatttac atctgcttgg tcgtgctgat gttgtgttgt     840
aatttgtaaa aagcagattg aagttcggta cagtatatta tcgtgaacct ataaaaaaaa     900
aaaaaaaaaa aaaaaaaaaa aaaaaa                                           926

<210> SEQ ID NO 5
<211> LENGTH: 3845
<212> TYPE: DNA
<213> ORGANISM: Zea mays
<220> FEATURE:
<221> NAME/KEY: unsure
<222> LOCATION: (722)...(722)
<223> OTHER INFORMATION: n = A, C, G or T

<400> SEQUENCE: 5
cagcttcggc ttgcaaggtg cgtggtacca gtaatatata tcaatcaagt tcagcaacca      60
tgatgcatgc atccacatac tactttcttt gtttgcttgc ccgccccacgg tcacggctta     120 attacaaatg aaatccgcgc aggatgagtg ggtggtctgt cgtgtgttca acaagaccac     180
cgggatcaag aagacggctg cgccggcata ccaggtggcc atggccggtg ctgagatgga     240
tcagaatcag aacaacattc cggccatccc catccccatg ccgctgcagc tgccactgcc     300
cgtgcccatg cagatgcaat tcccatcct gccagatttt gtcatggacc cggtggcccc     360
ctactacccc aacccaaatg ccggcgccgg gatgatgccg cctatggcgg ccggtattgg     420
cggcgccggc gggctccaga tcaacggcgc cctgttcggc aatccgatgc ccgcgccgct     480
gccgatgaac ttctaccacc accagatggg catggggca gcagctggcc aggtggacat     540
gggggcagcg gctggccaga tggacatggg agcagctggc gctggcgctg gcggcttcga     600
cgttgcagcg ccggagagta ggccgtcctc gatggtgtca cagaaggacg aacaggctaa     660
tgccgctgag atctcgtcga tgatgtctgt gaccggccca gggtccgcga ccaccaccat     720
angagatgga tggcatatgg aagtacaagt actgaaaaag tgaaatgga gtttggagac     780 aaatgcatga attcggcatg aatatgcatg ttatatctac tatatctgca ttgcattttg     840 tgaaatttg catggttcct atatttctgc aataactagt cggtaagata tgtgtgcatg     900
catgtgctag tatatacatg cattgtatca ttgcatgtgt ggtatatgtg tgtgtcgttt     960
```

```
ggtcttagta atccggggca tgatggtacc catacctgga tttacatctg cttgggcgtg    1020
ctgatgttgt gttgtaattt gtaaaaagca gattgaagtt cggtacagta tattatcgtg    1080
aacctatata tattatactt gtgtgaatga gtagtatgttg tttaatttat ttatgaactt   1140
gattgcgaaa ttaaacttta aattgtatgt atttaaattg taatcttttt tgttaaggct    1200
acttaccaaa tatgtatgtg atagttgtca cgcctgcata cttttgcggc gccgaatagg    1260
aacaaaacaa atcctacggc gctggctcaa tcttatattc gctttctatc aataatagct    1320
tgtaacacgt tttcctaacc caccccaccc caataaccc ccacgttcga tccgtgcact    1380
ccatatctaa accatcaact cttcatgaga taggttgtcc tcctccgaac ttaagcatgt    1440
cggggctacg attctcatgg ttacgaccca cacatatata gagtggtttt aagggaggct    1500
ggttcccgat agttgaagaa gtgtgagggt gtgagatttc aagtagtttg tattggtgtc    1560
aaaaaaggag gctagcgacg gtttgccact agagttatgc gagatacaca tgtgtggtgg    1620
atactagcga gcgtatgacc tcctttatta gtgtgttgga gagcgttgtg aaggatcatg    1680
catacggtgg gcggtatggt acaggttgcc ggtaacacag attgccaaca atagttataa    1740
tattatttat atcctaatca tttctttttt gtctacaaga tatatggttg tgcattatag    1800
gtacatcctt ctagaaaagt tcaattgtta gcagctacac tgtttcattt gtttgtcctc    1860
ctttgtttct cttttgtttc catttaaagg gattctatag atagtgccca tgaagtcgct    1920
ggcactaaca ctaccggaga cgcgttcttt gccgagtgct caaagcttta ccgagtgcaa    1980
aatctcgggc tctcggcaaa gaatactttg tcgagcgcca ctctcggcga accatggcac    2040
tcggcaaaga cgactgtgcc ctgtgtaaag cactcgacat acaaagacgc tcgaataagg    2100
cggatttgcc gagtgtcggt ctctcgtcac aacgagacac tcgacaaagc gccatcagca    2160
gccgtctaca gttgatggcc attaactatg ccgagtacca ggaaaggaca ctcggtaaag    2220
ttatgtcttt gtcgagtgtc acccactcac cctcatacac tcggctatcc catgacactc    2280
ggcaaagtat atttttttc tttttcccca aactttttta tggtgtgttt ctacaatata    2340
tagacttaca tgttcgattt tggcacaagt atcaaagtgt ttgctataac aattgggtaa    2400
gatatgtgtg catgcatgtg ctagtatata catgcattgt atcattgcat gtgtggtata    2460
tgtgtgtgtc atttggtctt agtaatccgg ggcatgcatg atggtacgca tacctggatt    2520
tacatctgct tggtcgtgct gattgttgcg ttgtaacttg taagaagcag attgaagttc    2580
ggtacagtat attatcgtga acctatatat attatacatg tgtgaatgat agtatgttgt    2640
ttaattttat gaacttgatt gccaaattaa actttaaaaa tgtatgcatt taaattgtaa    2700
tcttttttct taaggctact taccaaatat gtatgtgata gttgtcacgc ctacatactt    2760
tttgtggcgc ccggatagga acaaaacaaa tcctgcggcg ctggctcaac cttatattcg    2820
ctttctatca ataacagctt gtaacacgtt tttctgaccc accccacccc caataaccc    2880 cacacccgac ccgtgcactc catatgtaaa ccatcaactc ttcatgaggt aggttgtcct    2940
ccttcgaact taagcatgtc ggggctacga ttctcgtgtg tgtgtgtgtg tgtgtatata    3000
tatgaggctg gttcaccgat agttgaggag gaagtgtgag ggtgtgagat ttgaagtagt    3060
ttgcattgat gtcaaaaaag aggctagcga tgatttgtca gtagagttat gcagatcag     3120 cagatgtggt ggatactagc gagcgtgtga cctcctttat tagcggattg gagagcgttg    3180
tgaaggatca tgcatacggt gggcggtatg gtagaggttg tcggtaacac ggattgccaa    3240
aaatatttat aatattattt atatcctaat tatttattttt ttgcctataa gatatatggt    3300
```

-continued

```
tgtgcattat agatacatcc ttctaggaaa gttcaattgt tagcggctac accgtttcat    3360
ttgtttgtcc tcctttcttt ctcttttgtt tccattcgaa gagattctgt ggacagtgcc    3420
catgaagtcg caggcactaa caatgaccta ggcaatccat aaggtgcccc cattgccctc    3480
cctttcctcc acccaatttt aatagcatat ttttcctccg cccgattctt gatagcataa    3540
ttttaacatg catcagagaa cggtattgtg ctaattaatg gaaattggga caaataggaa    3600
tgtcagcacc aagatacttt gatgccatga aatttagta ttcttagttt ggtgctggca     3660
tacaggggag caaactcaaa catatatagg aataagaata cataggctct aatgcaatgt    3720
cacgagggac aaatccttag tttctaggct tgtcaagcaa agtggtgatg cataatttgt    3780
ataagttaag gttcttccat ctaattttaa atacccttat ggattatttt gtctttacaa    3840
gctag                                                                3845
```

<210> SEQ ID NO 6
<211> LENGTH: 391
<212> TYPE: PRT
<213> ORGANISM: Zea mays

<400> SEQUENCE: 6

```
Met Ala Asp Gln Gln Gln Pro Gln Gln Gln Pro Gln Glu Met Asp Val
 1               5                  10                  15

Asp Arg Thr Gly Gly Leu Glu Leu Pro Pro Gly Phe Arg Phe His Pro
            20                  25                  30

Ser Asp Phe Glu Ile Ile Asn Asp Tyr Leu Thr Lys Lys Val His Asp
        35                  40                  45

Arg Asp Tyr Ser Cys Ile Ala Ile Ala Asp Ala Asp Leu Asn Lys Thr
    50                  55                  60

Glu Pro Trp Asp Leu Pro Lys Val Ala Lys Met Gly Glu Lys Glu Trp
65                  70                  75                  80

Cys Phe Phe Tyr Gln Lys Asp Arg Lys Tyr Pro Thr Gly Leu Arg Ala
                85                  90                  95

Asn Arg Ala Thr Glu Ala Gly Tyr Trp Lys Ala Thr Gly Lys Asp Lys
            100                 105                 110

Glu Val Tyr Asn Pro Phe Ala Ala Glu Gly Leu Leu Leu Val Gly Met
        115                 120                 125

Lys Lys Thr Leu Val Phe Tyr Lys Gly Arg Ala Pro Arg Gly Asp Lys
    130                 135                 140

Thr Asn Trp Val Met His Glu Tyr Arg Leu Glu Gly Ser Gly Arg Leu
145                 150                 155                 160

Pro Ala Ser Pro Ala Ser Ala Ser Gly Ser Ala Thr Asn Ile Ala Ala
                165                 170                 175

Ala Met Met Lys Ala Ser Ala Ser Ala Cys Lys Asp Glu Trp Val Val
            180                 185                 190

Cys Arg Val Phe Asn Lys Thr Thr Gly Ile Lys Lys Thr Ala Ala Pro
        195                 200                 205

Ala Tyr Gln Val Ala Met Ala Gly Pro Glu Met Asp Gln Asn Gln Asn
    210                 215                 220

Asn Ile Pro Ala Ile Pro Ile Pro Met Pro Leu Gln Leu Pro Leu Pro
225                 230                 235                 240

Val Pro Met Gln Met Gln Phe Pro Ile Leu Pro Asp Phe Ala Met Asp
                245                 250                 255

Pro Val Ala Pro Tyr Tyr Pro Asn Pro Asn Ala Gly Ala Gly Met Met
            260                 265                 270
```

-continued

```
            Pro Pro Met Ala Leu Ala Gly Met Gly Gly Ala Gly Gly Leu Gln Ile
                275                 280                 285

Asn Gly Ala Leu Phe Gly Asn Pro Val Pro Ala Pro Leu Pro Met Asn
                290                 295                 300

Phe Tyr His His Gln Met Gly Met Gly Ala Ala Ala Gly Gln Val Asp
            305                 310                 315                 320

Met Gly Ala Ala Ala Gly Gln Met Asp Met Gly Ala Ala Gly Ala Gly
                            325                 330                 335

Ala Gly Gly Phe Asp Val Ala Ala Pro Glu Ser Arg Pro Ser Ser Met
                        340                 345                 350

Val Ser Gln Lys Asp Glu Gln Ala Asn Ala Ala Glu Ile Ser Ser Met
                    355                 360                 365

Met Ser Val Thr Gly Pro Gly Ser Ala Thr Thr Thr Ile Glu Met Asp
                370                 375                 380

Gly Ile Trp Lys Tyr Lys Tyr
            385                 390

<210> SEQ ID NO 7
            <211> LENGTH: 1618
            <212> TYPE: DNA
            <213> ORGANISM: Zea mays

<400> SEQUENCE: 7
gcgagcgagt gagagaccta gctagactga ccggcggccg ccggcaggcc gagaacgaag     60
cgtttgtgca ttgaaggagc aggagccatg gcggaccagc agcagccaca gcagcagccg    120
caggagatgg acgttgaccg taccggtggc ctcgaactgc tccagggtt ccgcttccac     180 ccgagcgact ttgagattat caacgactac ctcacgaaga aggtgcacga cagggactac    240
agctgcatcg ccatcgcgga cgccgaccta aacaagaccg agccatggga cctcccgaaa    300
gttgcaaaga tgggcgagaa ggagtggtgc ttcttctacc agaaggaccg caagtacccg    360
acggggctga gggcgaaccg ggccactgag gcgggttatt ggaaggcgac cggcaaggac    420
aaggaggtct acaaccccctt tgcagcggaa gggctgctgc tggtcggcat gaagaagacg    480
ctcgtgttct acaaaggcag ggctcccagg ggtgacaaaa ccaactgggt gatgcacgag    540
tacaggctcg aaggcagcgg taggctccct gctagtcctg catccgcatc cggctcagcc    600
accaacatcg ctgcggccat gatgaaagct tcagcttcgg cttgcaagga tgagtgggtg    660
gtctgtcgtg tgttcaacaa gaccaccggg atcaagaaga cggctgcgcc ggcataccag    720
gtggccatgg ccggtcctga gatggatcag aatcagaaca acattccggc catccccatc    780
cccatgccgc tgcagctgcc actgcccgtg cccatgcaga tgcaatttcc catcctgcca    840 gatttttgcca tggacccggt ggccccctac taccccaacc cgaatgccgg cgcggggatg    900
atgccgccta tggcattggc aggtatgggt ggcgccggcg ggctccagat caacggcgct    960
ctgttcggca atccggtgcc cgcgccgctg ccgatgaact tctaccacca ccagatgggc   1020 atggggcag cagctggcca ggtggacatg ggggcagcgg ctggccagat ggacatggga   1080
gcagctggcg ctggcgctgg cggcttcgac gttgcagcgc cggagagtag gccgtcctcg   1140
atggtgtcac agaaggacga acaggctaat gccgccgaga tctcgtcgat gatgtctgtg   1200
accggcccag gtccgcgac caccaccata gagatggatg gcatatggaa gtacaagtac   1260
tgaaaaagtg gatatggagt ttggagacaa atgcatgaat atgcatgtta tatctactat   1320
atctgcattg cattttgtga aaatttgcat ggttcctata tttctgcaat aactagtcgg   1380
taagatatgt gtgcatgcat gtgctagtat atacatgcat tgtatcattg catgtgtggt   1440
```

```
atatgtgtgt gtcgtttggt cttagtaatc cggggcatga tggtacccat acctggattt    1500
acatctgctt ggtcgtgctg atgttgtgtt gtaatttgta aaaagcagat tgaagttcgg    1560
tacagtatat tatcgtgaac ctataaaaaa aaaaaaaaaa aaaaaaaaaa aaaaaaa       1618

<210> SEQ ID NO 8
<211> LENGTH: 769
<212> TYPE: DNA
<213> ORGANISM: Zea mays

<400> SEQUENCE: 8
gcgagcgagt gagagaccta gctagactga ccggcggccg ccggcaggcc gagaacgaag      60
cgtttgtgca ttgaaggagc aggagccatg gcggaccagc agcagccaca gcagcagccg     120
caggagatgg acgttgaccg taccggtggc ctcgaactgc ctccagggtt ccgcttccac     180
ccgagcgact ttgagattat caacgactac ctcacgaaga aggtgcacga cagggactac     240
agctgcatcg ccatcgcgga cgccgaccta aacaagaccg agccatggga cctcccgaaa     300
gttgcaaaga tgggcgagaa ggagtggtgc ttcttctacc agaaggaccg caagtacccg     360
acggggctga gggcgaaccg ggccactgag gcgggttatt ggaaggcgac cggcaaggac     420
aaggaggtct acaaccccttt tgcagcggaa gggctgctgc tggtcggcat gaagaagacg     480
ctcgtgttct acaaaggcag ggctcccagg ggtgacaaaa ccaactgggt gatgcacgag     540
tacaggctcg aaggcagcgg taggctccct gctagtcctg catccgcatc cggctcagcc     600
accaacatcg ctgcggccat gatgaaagct tcagcttcgg cttgcaagga tgagtgggtg     660
gtctgtcgtg tgttcaacaa gaccaccggg atcaagaaga cggctgcgcc ggcataccag     720
gtggccatgg ccggtcctga gatggatcag aatcagaaca acattccgg                 769

<210> SEQ ID NO 9
<211> LENGTH: 16
<212> TYPE: DNA
<213> ORGANISM: Artificial Sequence
<220> FEATURE:
<223> OTHER INFORMATION: primer

<400> SEQUENCE: 9
gcatatggaa gtacaa                                                      16

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
gcaatgcaga tatagtag                                                    18
```